US011369335B2

(12) United States Patent
Nakano et al.

(10) Patent No.: US 11,369,335 B2
(45) Date of Patent: Jun. 28, 2022

(54) RADIATION IMAGE DETECTION DEVICE

(71) Applicant: Konica Minolta Inc., Tokyo (JP)

(72) Inventors: Hiroaki Nakano, Sagamihara (JP);
Naoki Hayashi, Higashimurayama (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 16/869,171

(22) Filed: May 7, 2020

(65) Prior Publication Data

US 2020/0367852 A1 Nov. 26, 2020

(30) Foreign Application Priority Data

May 22, 2019 (JP) .............................. JP2019-095995

(51) Int. Cl.
*A61B 6/00* (2006.01)
*H04N 5/32* (2006.01)

(52) U.S. Cl.
CPC ............ *A61B 6/566* (2013.01); *A61B 6/4283* (2013.01); *H04N 5/32* (2013.01)

(58) Field of Classification Search
CPC ......... A61B 6/566; A61B 6/4283; H04N 5/32
See application file for complete search history.

(56) References Cited

U.S. PATENT DOCUMENTS

| 6,127,684 | A * | 10/2000 | Kaifu ....................... H04N 5/32 |
| | | | 250/208.1 |
| 6,448,561 | B1 * | 9/2002 | Kaifu ..................... H04N 5/235 |
| | | | 250/370.09 |
| 6,542,579 | B1 * | 4/2003 | Takasawa ................ A61B 6/00 |
| | | | 378/162 |
| 6,671,394 | B1 * | 12/2003 | Sako ...................... A61B 6/465 |
| | | | 250/370.09 |
| 6,762,429 | B2 * | 7/2004 | Aonuma ................ A61B 6/463 |
| | | | 250/583 |
| 6,795,572 | B1 * | 9/2004 | Matsuno ................... G01T 1/17 |
| | | | 382/132 |
| 7,197,112 | B2 * | 3/2007 | Maschke .............. A61B 6/4429 |
| | | | 378/116 |

(Continued)

FOREIGN PATENT DOCUMENTS

| JP | 11-160439 A | 6/1999 |
| JP | 2004-184679 A | 7/2004 |
| WO | 2009/031411 A1 | 3/2009 |

*Primary Examiner* — David P Porta
*Assistant Examiner* — Djura Malevic
(74) *Attorney, Agent, or Firm* — Rankin, Hill & Clark LLP

(57) ABSTRACT

Provided is a radiation image detection device used in a radiation image photographing system including the radiation image detection device that is portable and acquires radiation image data based on irradiated radiation, and a plurality of control terminals that are connected to the radiation image detection device and acquire the radiation image data acquired by the radiation image detection device, the radiation image detection device includes a hardware processor that: transmits and receives communication information to and from each of the control terminals; determines whether an IP address to be used for data communication by a connected one of the control terminals is a dynamic IP address or a static IP address, based on initial information received from each of the control terminals before data communication is established; and acquires an IP address, in accordance with a determination result.

4 Claims, 5 Drawing Sheets

(56) References Cited

U.S. PATENT DOCUMENTS

| | | | | |
|---|---|---|---|---|
| 7,592,577 | B1* | 9/2009 | Liu | H01L 27/1463 250/208.1 |
| 8,275,835 | B2* | 9/2012 | Eguchi | A61B 6/4494 709/204 |
| 9,134,436 | B2* | 9/2015 | Kwak | A61B 6/547 |
| 9,462,990 | B2* | 10/2016 | Kuwabara | A61B 6/542 |
| 9,788,809 | B2* | 10/2017 | Hiroike | A61B 6/54 |
| 10,039,509 | B2* | 8/2018 | Okusu | A61B 6/4208 |
| 10,045,751 | B2* | 8/2018 | Okusu | A61B 6/46 |
| 10,159,455 | B2* | 12/2018 | Takanaka | H05G 1/58 |
| 10,285,660 | B2* | 5/2019 | Zaiki | A61B 6/4429 |
| 10,368,823 | B2* | 8/2019 | Uchiyama | A61B 6/4266 |
| 10,368,826 | B2* | 8/2019 | Tamura | A61B 6/4233 |
| 10,485,505 | B2* | 11/2019 | Yamada | A61B 6/5241 |
| 10,531,856 | B2* | 1/2020 | Hiroike | A61B 6/542 |
| 10,605,747 | B2* | 3/2020 | Ubukata | G01T 1/17 |
| 10,617,379 | B2* | 4/2020 | Hiroike | A61B 6/4233 |
| 10,682,105 | B2* | 6/2020 | Shimizukawa | A61B 6/4411 |
| 10,695,024 | B2* | 6/2020 | Miyamoto | H04N 5/367 |
| 10,856,833 | B2* | 12/2020 | Niwa | A61B 6/563 |
| 10,925,570 | B2* | 2/2021 | Xiao | A61B 6/465 |
| 10,952,697 | B2* | 3/2021 | Lalena | A61B 6/465 |
| 2003/0086523 | A1* | 5/2003 | Tashiro | A61B 6/4233 378/19 |
| 2003/0142119 | A1* | 7/2003 | Akagi | A61B 6/4283 345/698 |
| 2004/0086163 | A1* | 5/2004 | Moriyama | A61B 6/566 382/131 |
| 2004/0114725 | A1* | 6/2004 | Yamamoto | H04L 67/12 378/189 |
| 2004/0190780 | A1* | 9/2004 | Shiihashi | A61B 6/4494 382/210 |
| 2004/0258204 | A1* | 12/2004 | Nokita | A61B 6/585 378/91 |
| 2005/0213702 | A1* | 9/2005 | Akagi | A61B 6/4494 378/37 |
| 2006/0074983 | A1* | 4/2006 | Jones | G16H 10/65 |
| 2006/0080143 | A1* | 4/2006 | Tsuchino | G16H 40/40 705/2 |
| 2006/0094936 | A1* | 5/2006 | Russ | H04M 1/72409 600/300 |
| 2007/0170239 | A1* | 7/2007 | Hartman | G06Q 20/3574 235/375 |
| 2007/0253531 | A1* | 11/2007 | Okuzawa | G06T 5/009 378/62 |
| 2008/0049901 | A1* | 2/2008 | Tamakoshi | A61B 6/566 378/98.2 |
| 2009/0108311 | A1* | 4/2009 | Liu | H01L 27/14609 257/294 |
| 2009/0109313 | A1* | 4/2009 | Liu | H04N 5/32 348/308 |
| 2009/0116710 | A1* | 5/2009 | Futami | G16H 30/20 382/128 |
| 2010/0102241 | A1* | 4/2010 | Zeller | H04N 5/32 250/370.09 |
| 2010/0104065 | A1* | 4/2010 | Eguchi | A61B 6/4233 378/62 |
| 2010/0132033 | A1* | 5/2010 | Lu | H04L 63/08 726/15 |
| 2010/0169423 | A1* | 7/2010 | Eguchi | A61B 6/4405 709/204 |
| 2010/0187427 | A1* | 7/2010 | Kuwabara | A61B 6/542 250/370.08 |
| 2010/0207032 | A1* | 8/2010 | Tsubota | G01T 1/17 250/370.09 |
| 2011/0111703 | A1* | 5/2011 | Claverie | H04N 5/32 455/66.1 |
| 2012/0018641 | A1* | 1/2012 | Watanabe | A61B 6/563 250/354.1 |
| 2012/0134474 | A1* | 5/2012 | Duca | A61B 6/4233 378/96 |
| 2012/0163542 | A1* | 6/2012 | Kitano | A61B 6/548 378/91 |
| 2012/0166607 | A1* | 6/2012 | Kitano | A61B 6/4233 709/223 |
| 2012/0206233 | A1* | 8/2012 | Kamiya | A61B 6/4283 340/2.1 |
| 2012/0208576 | A1* | 8/2012 | Kamiya | A61B 6/4283 455/500 |
| 2013/0136234 | A1* | 5/2013 | Noma | H05G 1/64 378/91 |
| 2013/0185096 | A1* | 7/2013 | Giusti | G16H 20/40 705/3 |
| 2013/0201316 | A1* | 8/2013 | Binder | H04L 67/12 348/77 |
| 2013/0208860 | A1* | 8/2013 | Sugizaki | A61B 6/542 378/62 |
| 2013/0301802 | A1* | 11/2013 | Eguchi | H05G 1/08 378/98 |
| 2014/0072103 | A1* | 3/2014 | Kitano | A61B 6/4233 378/62 |
| 2014/0211922 | A1* | 7/2014 | Kuwabara | A61B 6/56 378/97 |
| 2014/0254760 | A1* | 9/2014 | Hiroike | A61B 6/4233 378/62 |
| 2015/0146862 | A1* | 5/2015 | Kim | A61B 6/4411 378/91 |
| 2015/0146863 | A1* | 5/2015 | Kim | A61B 6/566 378/91 |
| 2015/0149195 | A1* | 5/2015 | Rose | H04L 65/4015 705/2 |
| 2015/0177387 | A1* | 6/2015 | Exelmans | A61B 6/4233 378/98 |
| 2015/0320365 | A1* | 11/2015 | Schulze | A61B 5/7282 600/408 |
| 2016/0015341 | A1* | 1/2016 | Lee | G01T 1/17 250/395 |
| 2016/0081650 | A1* | 3/2016 | Okusu | A61B 6/4208 378/62 |
| 2016/0183038 | A1* | 6/2016 | Govaerts | H04W 12/50 455/41.1 |
| 2016/0210424 | A1* | 7/2016 | Di Battista | G06Q 10/0631 |
| 2017/0168812 | A1* | 6/2017 | Golay | G06F 8/654 |
| 2018/0000442 | A1* | 1/2018 | Hiroike | A61B 6/54 |
| 2019/0231299 | A1* | 8/2019 | Lalena | A61B 6/563 |
| 2021/0033543 | A1* | 2/2021 | Kuwata | G01N 23/04 |

\* cited by examiner

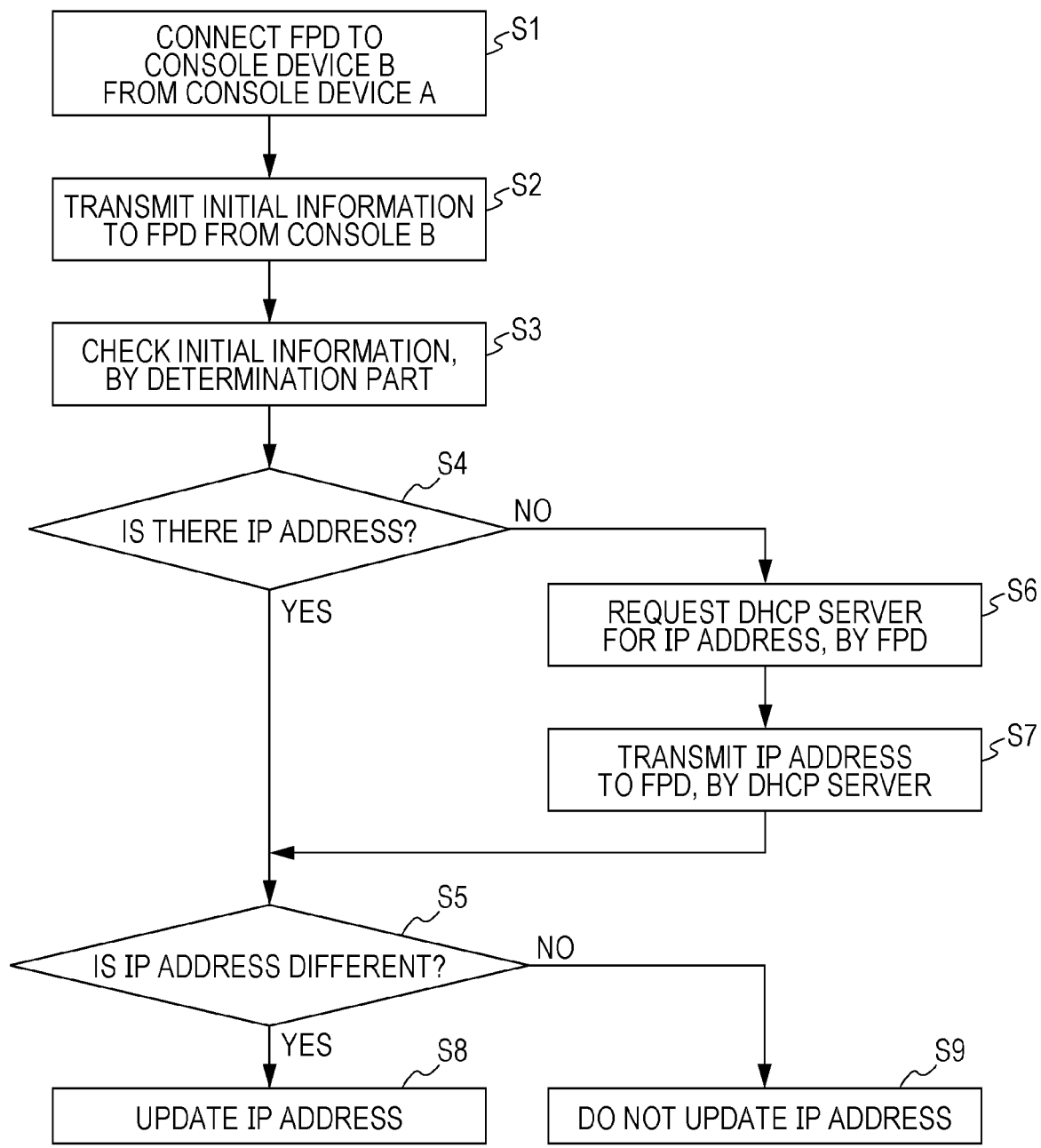

RADIATION IMAGE DETECTION DEVICE

The entire disclosure of Japanese patent Application No. 2019-095995, filed on May 22, 2019, is incorporated herein by reference in its entirety.

BACKGROUND

Technological Field

The present invention relates to a portable radiation image detection device used in a radiation image photographing system.

Description of the Related Art

In recent years, in the medical field, a portable X-ray image detection device called a flat panel detector (FPD) has been frequently used (e.g., see JP 2004-184679 A and JP H11-160439 A). The FPD is connectable to a console device, and an X-ray image detected and recorded by the FPD is displayed by the console device.

The FPD includes a conversion part that converts X-rays detected by a radiation detecting element into an electric signal, an A/D converter that digitizes the converted electrical signal, an output part that outputs the digitized signal to a console device as a photographed image, a battery that supplies power to these parts, and the lie.

The console device is a computer that mainly performs: control of radiation image photographing (e.g., radiography); display of X-ray images acquired from the FPD; and instruction such as image processing contents for such X-ray image data. The console device includes a processor, an operation input part such as a mouse and a keyboard, and a display part such as a liquid crystal display (LCD), and performs the control, display, instruction, and the like described above through various screens such as a menu screen displayed on the display part.

Re-publication of PCT International Publication No. 2009/031411 discloses a technique for wirelessly connecting an FPD and a console device. A radiographic image capturing system disclosed in Re-publication of PCT International Publication No. 2009/031411 associates an access point or a router to a console device in advance, and switches a connection target when recognizing that the access point is different. This can eliminate an operation of wired connection, and therefore can reduce an operation load when roaming the FPD in the radiographic image capturing system disclosed in Re-publication of PCT International Publication No. 2009/031411.

Meanwhile, in medical device development in recent years, there is much collaboration and cooperation between companies by business to business (B to B), and system configurations by a combination of multi-vendors are increasing.

For example, the system configurations are being diversified in general radiography, for example, an X-ray irradiation device that irradiates X-rays is manufactured by Company A, an FPD that receives X-rays is by Company B, a console device that receives images from the FPD is by Company C, and picture archiving and communication systems (PACS) that store images is by Company D.

On the other hand, large-scale hospitals and the like have a plurality of photographing rooms, and properly use the photographing rooms in accordance with the purpose of photographing. Therefore, a situation arises in which a console device of Company X is used in a photographing room A, while a console device of Company Y is used in a photographing room B. In such a situation, there is a case where it is desired to generally use an FPD of Company X. In this case, the FPD of Company X needs to be usable on the console device of Company Y, and the cooperation is made possible by providing a built-in module called "software development kit (SDK)" from Company X to Company Y as a cooperation kit. This realizes sharing (or roaming) of one FPD between a plurality of photographing rooms provided with console devices of different systems.

In sharing an FPD between a plurality of systems having different settings for each system, it is required to adjust FPD settings when connecting to a console device. There are various settings between the console device and the FPD, such as settings required for communication, as well as parameters required for photographing. Therefore, work of adjusting the FPD settings to the console device settings when connecting to the console device is a part that increases a burden on service personnel.

Whereas, as communication settings, there are cases of adopting a system that dynamically allocates IP addresses such as a dynamic host configuration protocol (DHCP), and there are systems that operate statically with a fixed IP address.

However, any environment uses a fixed IP in a fixed IP environment, and any environment uses a dynamic IP in a DHCP environment, for operation in a closed configuration in the system. Therefore, in a case of sharing a panel between systems, it has been required for service personnel to set the FPD again in accordance with the individual systems, or to provide limitation to inhibit sharing of the FPD.

SUMMARY

An object of the present invention is to provide a portable radiation image detection device that enables movement between a static IP environment and a dynamic IP environment and automatic setting of an IP address, without putting a burden on service personnel and a user (without awareness).

To achieve the abovementioned object, according to an aspect of the present invention, there is provided a radiation image detection device used in a radiation image photographing system including the radiation image detection device that is portable and acquires radiation image data based on irradiated radiation, and a plurality of control terminals that are connected to the radiation image detection device and acquire the radiation image data acquired by the radiation image detection device, and the radiation image detection device reflecting one aspect of the present invention comprises a hardware processor that: transmits and receives communication information to and from each of the control terminals; determines whether an IP address to be used for data communication by a connected one of the control terminals is a dynamic IP address or a static IP address, based on initial information received from each of the control terminals before data communication is established; and acquires an IP address, in accordance with a determination result.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention:

FIG. 5 is a flowchart for explaining an IP address automatic setting process according to the embodiment.

DETAILED DESCRIPTION OF EMBODIMENTS

Hereinafter, one or more embodiments of the present invention will be described with reference to the drawings. However, the scope of the invention is not limited to the disclosed embodiments.

<1> System Configuration

Figure 1:
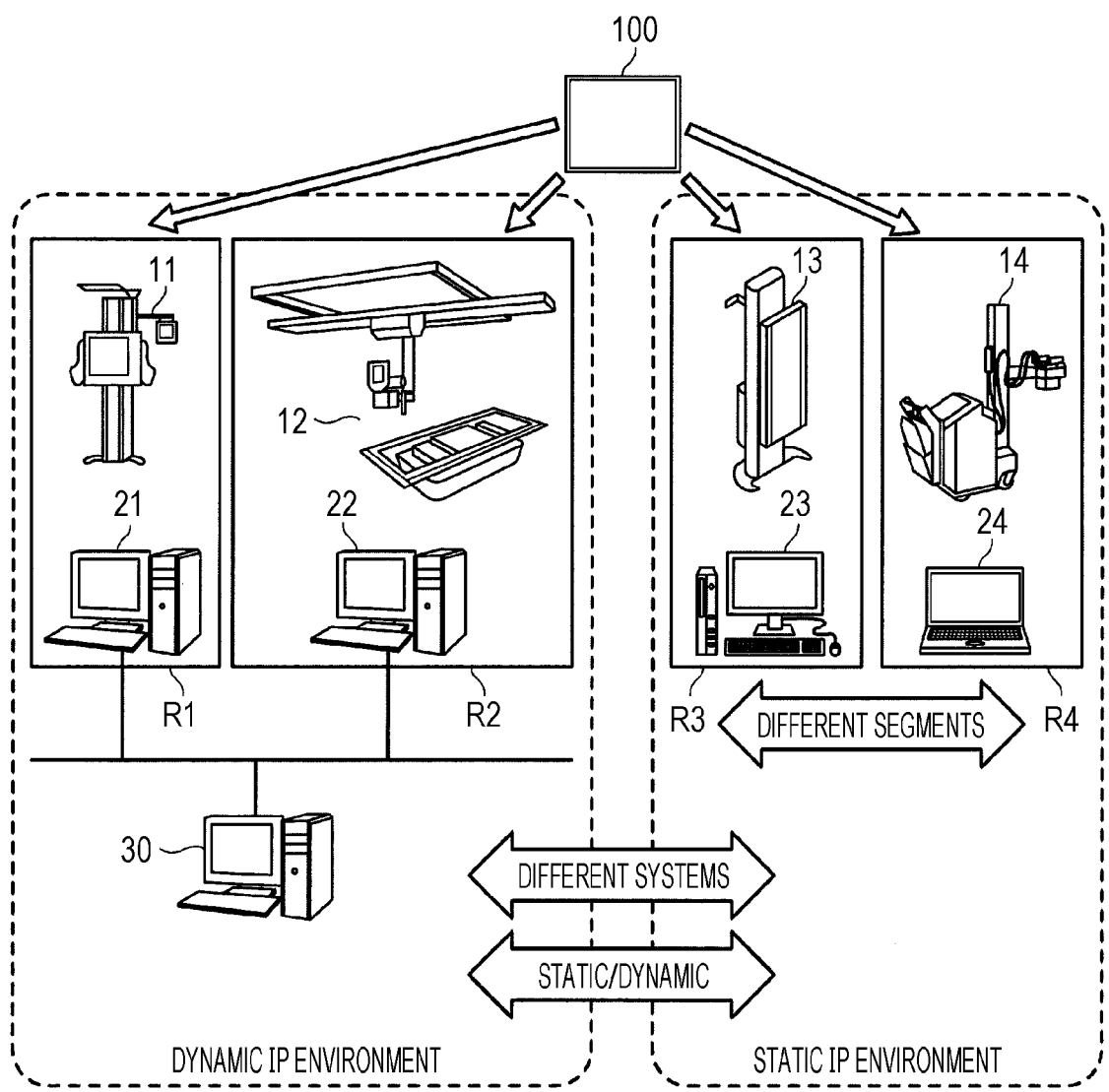
FIG. 1 is a diagram showing a configuration of a radiation image photographing system assumed in an embodiment.

FIG. 1 shows a configuration example of a radiation image photographing system assumed in the present embodiment.

Radiation photographing devices 11, 12, 13, and 14 and console devices 21, 22, 23, and 24 are provided in respective photographing rooms R1, R2, R3, and R4. Among the photographing rooms R1, R2, R3, and R4, the photographing rooms R1 and R2 are under a dynamic environment, and the photographing rooms R3 and R4 are under a static environment.

In each of the photographing rooms R1 to R4, the radiation photographing devices 11 to 14 and the console devices 21 to 24 are connected by a communication cable (not shown) or the like. The console devices 21 to 24 performs setting of photographing conditions of the radiation photographing devices 11 to 14 and an FPD 100, image analysis of radiation images obtained by the radiation photographing devices 11 to 14 and the FPD 100, and the like.

The console devices 21 to 24 can be called control terminals of the radiation photographing devices 11 to 14 and the FPD 100.

A DHCP server 30 assigns an IP address to equipment provided in the dynamic IP environment and transmits the IP address by wire or wirelessly. At this time, the DHCP server 30 assigns IP addresses such that the IP addresses do not overlap.

The FPD 100 is portable. The FPD 100 is used by being mounted on panel-mounted radiation photographing devices 11, 12, and 13, such as the radiation photographing devices 11, 12, and 13 in the photographing rooms R1, R2, and R3. Further, for example, for a non-panel-mounted radiation photographing device 14 such as a radiation photographing device 14 in the photographing room R4, the FPD 100 is used at a position separated from the radiation photographing device 14. For example, when radiographic examination is performed in the photographing room R1, the FPD 100 is mounted to the radiation photographing device 11 in the photographing room R1. Next, for example, when radiographic examination is performed in the photographing room R3, the FPD 100 is removed from the radiation photographing device 11 in the photographing room R1, and is mounted to the radiation photographing device 13 in the photographing room R3. In addition, for example, when radiographic examination is performed in the photographing room R4 after radiographic examination in the photographing room R1, the FPD 100 removed from the radiation photographing device 11 in the photographing room R1 is brought into the photographing room R4 to be used.

When the FPD 100 is used in each of the photographing rooms R1 to R4, the FPD 100 communicates with the console devices 21 to 24 in the respective photographing rooms R1 to R4, and transmits a captured image to the console devices 21 to 24.

In this way, the FPD 100 is associated to the plurality of console devices 21 to 24, and is shared (roamed) by the plurality of console devices 21 to 24.

When the FPD 100 performs information communication with the console devices 21 to 24, an IP address ("10.14.xx.xx", "192.168.50.xx", "192.168.20.00" or the like in the figure) is required. Setting of the IP address will be described in detail below.

Note that any known configuration may be applied to the configurations of the radiation photographing devices 11, 12, 13, and 14 and the console devices 21 to 24, and a detailed description thereof will be omitted.

<2> FPD and Console Device According to Embodiment

Figure 2:
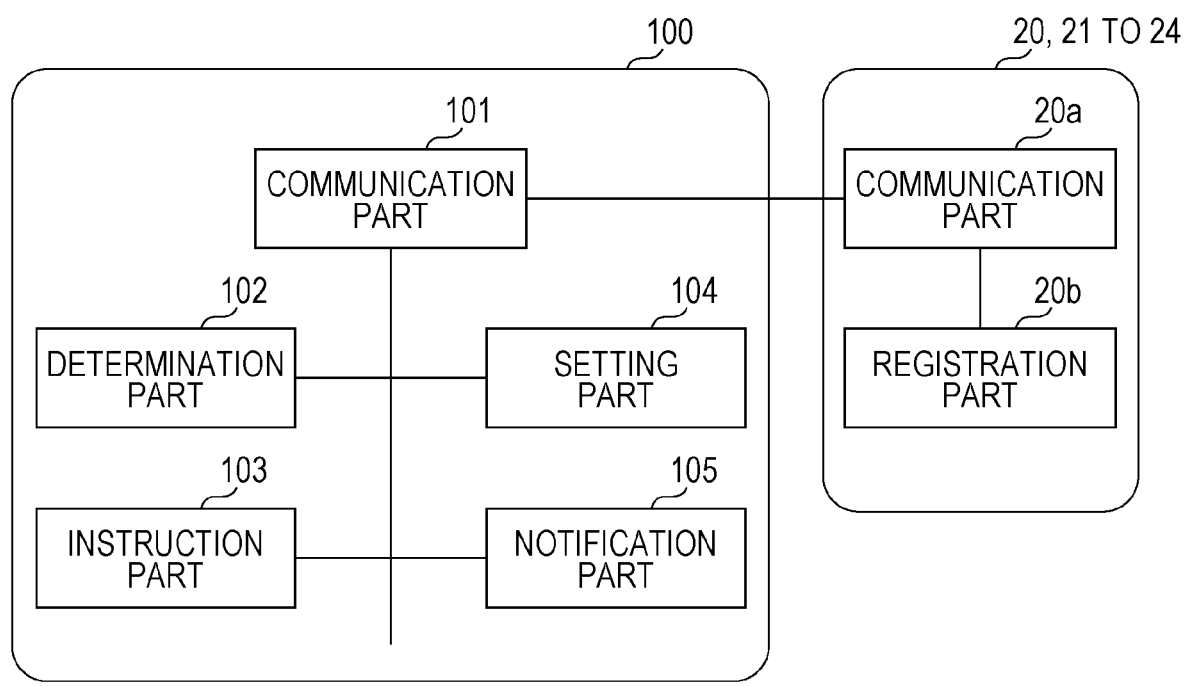
FIG. 2 is a block diagram showing a main configuration of an FPD and a console device according to the embodiment.

FIG. 2 is a block diagram showing a main configuration of the FPD 100 and a console device 20 (21 to 24) of the present embodiment.

Of course, the FPD 100 and the console device 20 have an original basic configuration of the FPD other than the configuration shown in FIG. 2.

In other words, as a basic configuration, the FPD 100 includes a conversion part that converts X-rays detected by a radiation detecting element into an electric signal, an A/D converter that digitizes the converted electrical signal, an output part that outputs the digitized signal to the console devices 21 to 24 as a photographed image, a battery that supplies power to these parts, and the like.

The console device 20 includes, as a basic configuration, a controller that controls radiation image photographing in the radiation photographing devices 11 to 14 and the FPD 100, a display part that displays a radiation image (e.g., an X-ray image) acquired from the FPD 100, an image processing part that performs image processing on the radiation image, and the like.

In addition to these basic configurations, as shown in FIG. 2, the FPD 100 includes a communication part 101, a determination part 102, an instruction part 103, a setting part 104, and a notification part 105. The console device 20 includes a communication part 20a and a registration part 20b.

The communication part 101 transmits and receives communication information to and from the console device (control terminal) 20. Further, the communication part 101 also transmits and receives communication information to and from the DHCP server 30.

The determination part 102 determines whether an IP address to be used for data communication by the connected console device 20 is a dynamic IP address or a static IP address, based on initial information received from the console device 20 before the data communication is established. Here, the initial information is, for example, information including communication mode information (that is, information indicating whether a dynamic IP address or a static IP address is used as a communication mode). When the console device 20 of a connection destination is a console device under a static environment, the initial information includes an IP address. On the other hand, when the console device 20 of a connection destination is a console device under a dynamic environment, the initial information does not include an IP address.

The instruction part 103 instructs the communication part 101 to acquire an IP address in accordance with a determination result of the determination part 102. For example, when a determination result that an IP address to be used for data communication in the console device 20 is a dynamic IP address is obtained in the determination part 102, the instruction part 103 instructs the communication part 101 to acquire an IP address from the DHCP server 30.

The setting part 104 performs update setting of an IP address in accordance with a determination result by the determination part 102 or an acquisition result of the IP address according to an instruction of the instruction part 103.

When the IP address is updated, the notification part 105 notifies a user of the fact. The notification part 105 is, for example, a light emitting diode (LED) provided on a surface of the FPD 100. Further, without limiting to this, the notification part 105 may give notification by other display, sound, light, mark, vibration, or the like.

Note that the processing by the communication part 101, the determination part 102, the instruction part 103, the setting part 104, and the notification part 105 may be realized by a computer including a central processing unit (CPU), a read only memory (ROM), and a random access memory (RAM) on the basis of a program. That is, the CPU reads a program according to processing contents from the ROM, develops the program in the RAM, and performs processing similar to that of the above-described communication part 101, determination part 102, instruction part 103, setting part 104, and notification part 105, in cooperation with the developed program.

Figure 3:
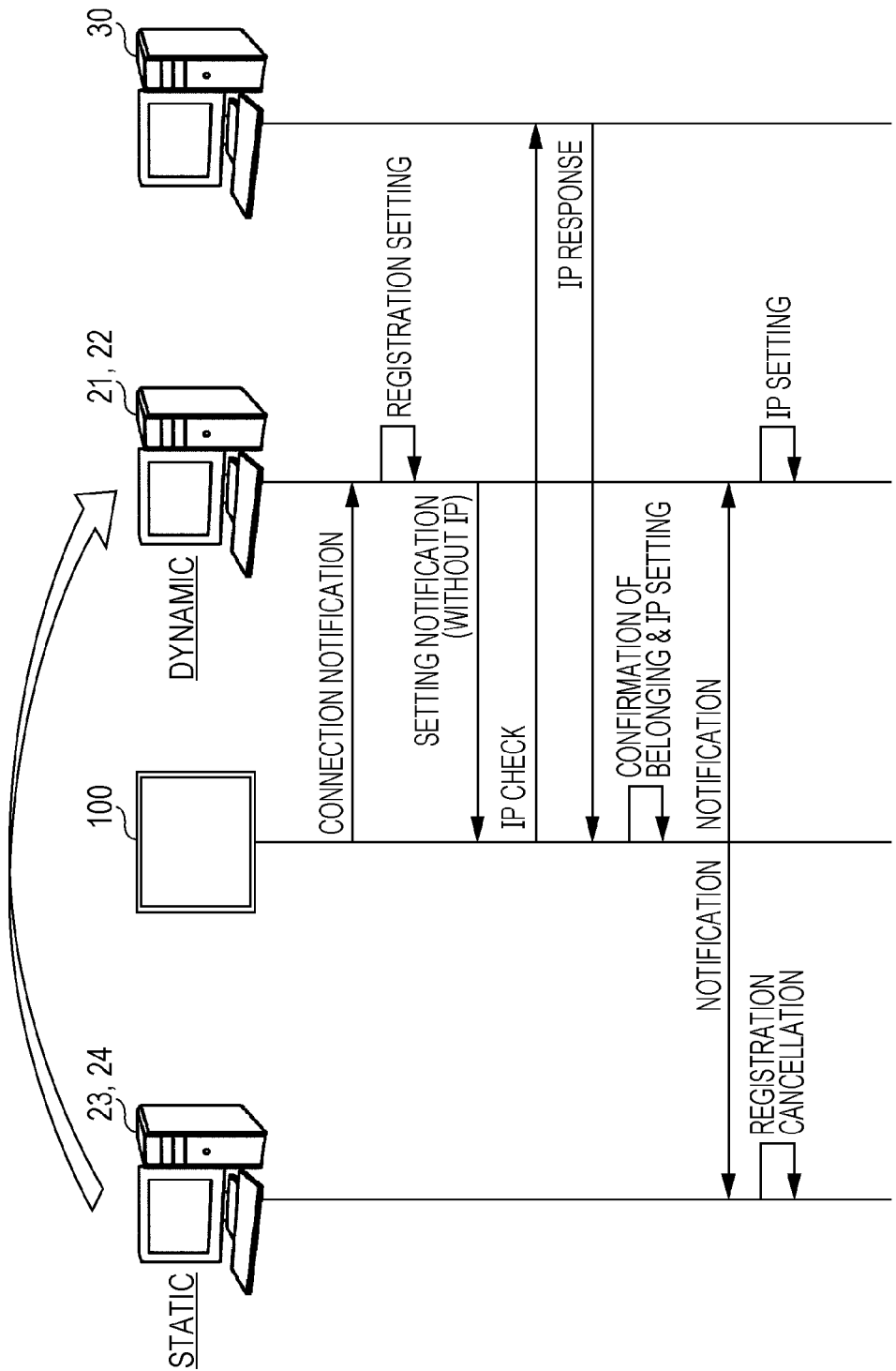
FIG. 3 is a sequence diagram showing an operation when the FPD is moved (that is, reconnected) from a console device under a static IP environment to a console device under a dynamic IP environment.
Figure 4:
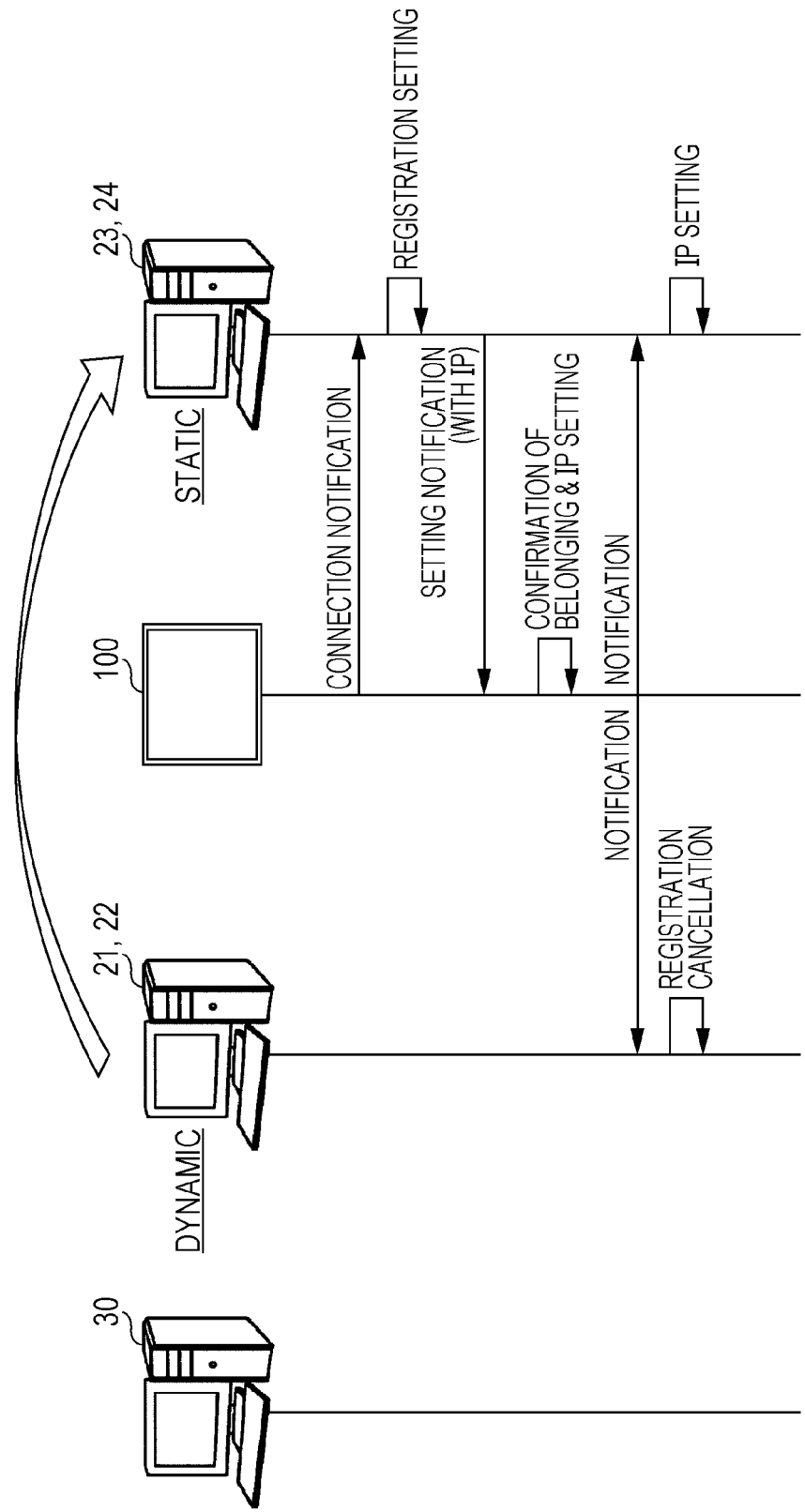
FIG. 4 is a sequence diagram showing an operation when the FPD is moved (that is, reconnected) from a console device under a dynamic IP environment to a console device under a static IP environment.

FIGS. 3 and 4 are sequence diagrams for explaining an operation of the present embodiment. FIG. 3 shows an operation when the FPD 100 is moved (that is, reconnected) from the console device 23 (24) under a static IP environment to the console device 21 (22) under a dynamic IP environment. FIG. 4 shows an operation when the FPD 100 is moved (that is, reconnected) from the console device 21 (22) under a dynamic IP environment to the console device 23 (24) under a static IP environment.

The operation of FIG. 3 will be described. First, the FPD 100 gives connection notification to the console device 21 (22) of a connection destination. The console device 21 (22) that has received the connection notification performs registration setting of the FPD 100 in the registration part 20b. Further, the console device 21 (22) transmits setting information (initial information) that does not include an IP address, to the FPD 100 that has transmitted the connection notification. Here, a reason why the setting information (initial information) does not include an IP address is that the console device 21 (22) is a console device under a dynamic IP environment.

Next, the FPD 100 checks an IP address with the DHCP server 30 (IP check). Then, the DHCP server 30 transmits the IP address to the FPD 100 (IP response).

Next, the FPD 100 that has received the IP address confirms the console device 21 (22) to which the FPD 100 belongs (confirmation of belonging), and sets the IP address (IP setting).

Next, the FPD 100 gives a notification to the console device 23 (24) to which the FPD 100 has previously belonged for canceling the registration, and gives a notification of the IP address to the console device 21 (22) to which the FPD 100 currently belongs. Upon receiving the notifications, the console device 23 (24) to which the FPD 100 has previously belonged cancels the registration of the FPD 100, and the console device 21 (22) to which the device currently belongs sets the same IP address as that of the FPD 100.

The operation of FIG. 4 will be described. First, the FPD 100 gives connection notification to the console device 23 (24) of a connection destination. The console device 23 (24) that has received the connection notification performs registration setting of the FPD 100 in the registration part 20b. Further, the console device 23 (24) transmits setting information (initial information) that includes an IP address, to the FPD 100 that has transmitted the connection notification. Here, a reason why the setting information (initial information) includes an IP address is that the console device 23 (24) is a console device under a static IP environment.

Next, the FPD 100 confirms the console device 23 (24) to which the FPD 100 belongs (confirmation of belonging), and sets its own IP address (IP setting) based on the IP address included in the initial information received from the console device 23 (24).

Next, the FPD 100 gives a notification to the console device 21 (22) to which the FPD 100 has previously belonged for canceling the registration, and gives a notification of the IP address to the console device 23 (24) to which the FPD 100 currently belongs. Upon receiving the notifications, the console device 21 (22) to which the FPD 100 has previously belonged cancels the registration of the FPD 100, and the console device 23 (24) to which the FPD 100 currently belongs sets the same IP address as that of the FPD 100.

FIG. 5 is a flowchart for explaining an IP address automatic setting process according to the present embodiment. Note that, in actual connection, the FPD 100 does not know, at an initial stage, whether console devices of an old connection destination and a new connection destination are a console device under a static environment or a console device under a dynamic environment. Therefore, in FIG. 5, the console device of the old connection destination is described as "console device A", and the console device of the new connection destination is described as "console device B".

When the FPD 100 is connected to the console device B from the console device A in step S1, the console device B transmits initial information to the FPD 100 in step S2.

Next, in step S3, the determination part 102 of the FPD 100 checks the initial information. In step S4, the determination part 102 determines whether or not the initial information includes an IP address. When it is determined that there is an IP address, the process proceeds to step S5.

On the other hand, when it is determined that there is no IP address, the process proceeds to step S6. In step S6, the FPD 100 requests the DHCP server 30 for an IP address. In response, in step S7, the DHCP server 30 transmits an IP address to the FPD 100. That is, when there is no IP address in the initial information, it can be determined that the console device B of the connection destination is a console device under a dynamic environment, and therefore an IP address is acquired from the DHCP server 30 in steps S6 and S7.

Next, in step S5, the determination part 102 determines whether or not the IP address is different. When it is determined that the IP address is different, the setting part 104 updates the IP address in step S8. On the other hand, when it is determined that the IP address is not different, the process proceeds to step S9, and the setting part 104 does not update the IP address.

Here, the update processing of the IP address is summarized as follows for each case. Case 1) When the received initial information has an IP address, and the IP address is the same as the existing setting, the IP address is not updated. Case 2) When the received initial information has an IP address, and the IP address is different from the existing setting, the IP address is updated. Case 3) When the received initial information has no IP address, and the IP address acquired from the DHCP server 30 is the same as the existing setting, the IP address is not updated. Case 4) When the received initial information has no IP address, and the IP address acquired from the DHCP server 30 is different from the existing setting, the IP address is updated.

Note that, in the example of FIG. 5, the acquisition of the IP address is selected based on whether or not the initial information includes the IP address, but the present invention is not limited to this. The acquisition of the IP address may be selected based on communication mode information included in the initial information.

For example, when the received communication mode information indicates "dynamic", the IP address is acquired from the DHCP server 30. On the other hand, when the received communication mode information is "static", the IP address included in the initial information is used.

As described above, according to the present embodiment, the FPD 100 includes: the communication part 101 that transmits and receives communication information to and from the console device 20; the determination part 102 that determines whether an IP address to be used for data communication by the connected console device 20 is a dynamic IP address or a static IP address, based on initial information received from the console device 20 before the data communication is established; and the instruction part 103 that instructs the communication part 101 to acquire an IP address in accordance with a determination result of the determination part 102. This makes it possible to realize the FPD 100 that enables movement of the FPD 100 between a static IP environment and a dynamic IP environment and automatic setting of an IP address, without putting a burden on service personnel and a user (without awareness).

That is, according to the FPD 100 of the present embodiment, when moving the FPD 100 between different console devices and under different environments, it is possible to assign an IP address appropriate for the environment without resetting or performing unnecessary communication or update processing, and allow a user to continue using the FPD 100 without awareness.

The above embodiment is merely an example of implementation in carrying out the present invention, and the technical scope of the present invention should not be construed in a limited manner by these. That is, the present invention can be implemented in various forms in a range without departing from the scope or main features of the present invention.

In the above-described embodiment, a case has been described where, when the IP address is updated, the notification part 105 of the FPD 100 notifies the user of the fact. In addition to this, the FPD 100 may notify the console device 20 and a cradle device (not shown) that the IP address has been updated, and the console device 20, the cradle device, and the like may notify that the IP address of the FPD 100 has been updated by display, a mark, light, sound, or the like.

In addition to the above-described embodiment, the user may be notified of a current setting state (e.g., whether or not the setting of the IP address has been completed). This notification may be exclusively performed by the FPD 100, or may be performed by the console device 20 or a cradle in addition to the FPD 100.

The present invention can be applied to, for example, an FPD used in an X-ray image photographing system.

Although embodiments of the present invention have been described and illustrated in detail, the disclosed embodiments are made for purposes of illustration and example only and not limitation. The scope of the present invention should be interpreted by terms of the appended claims.

What is claimed is:

1. A radiation image detection device used in a radiation image photographing system including the radiation image detection device that is portable and acquires radiation image data based on irradiated radiation, and a plurality of control terminals that are connected to the radiation image detection device and acquire the radiation image data acquired by the radiation image detection device, the radiation image detection device comprising
   a hardware processor that:
   transmits and receives communication information to and from each of the control terminals;
   determines whether an IP address to be used by a connected one of the control terminals for data communication is a dynamic IP address or a static IP address, based on initial information received from each of the control terminals before data communication is established; and
   acquires an IP address of the connected one of the control terminals, in accordance with a determination result,
   wherein, at the time of determining whether the IP address to be used by the connected one of the control terminals for data communication is a dynamic IP address or a static IP address, the hardware processor does not know whether the connected one of the control terminals is under a static environment or a dynamic environment,
   wherein, in a case where there is no IP address information in the initial information, the hardware processor determines that the IP address to be used by the connected one of the control terminals for data communication is a dynamic IP address, and
   wherein, in a case where there is IP address information in the initial information, the hardware processor determines that the IP address to be used by the connected one of the control terminals for data communication is a static IP address.

2. The radiation image detection device according to claim 1, wherein
   when a determination result that an IP address to be used for data communication in each of the control terminals is a dynamic IP address is obtained, the hardware processor acquires an IP address from a DHCP server.

3. The radiation image detection device according to claim 1, wherein
   when a determination result that an IP address to be used for data communication in each of the control terminals is a static IP address is obtained by the hardware processor, an IP address included in the initial information is used.

4. The radiation image detection device according to claim 1, wherein
   the hardware processor performs update setting of an IP address in accordance with a determination result, or an acquisition result of an IP address.

* * * * *